United States Patent [19]

Shelley

[11] Patent Number: 5,080,677
[45] Date of Patent: Jan. 14, 1992

[54] ACETABULAR COMPONENT OF HIP JOINT PROSTHESIS

[75] Inventor: Philip Shelley, Laughton Enlemouthern, Great Britain

[73] Assignee: Minnesota Mining and Manufacturing Company, St. Paul, Minn.

[21] Appl. No.: 611,311

[22] Filed: Nov. 13, 1990

Related U.S. Application Data

[63] Continuation of Ser. No. 394,742, Aug. 16, 1989, abandoned.

[30] Foreign Application Priority Data

Aug. 17, 1988 [GB] United Kingdom ............... 8819589

[51] Int. Cl.$^5$ .............................................. A61F 2/32
[52] U.S. Cl. ...................................................... 623/22
[58] Field of Search .................... 623/16, 18, 20, 22, 623/23

[56] References Cited

U.S. PATENT DOCUMENTS

| | | | |
|---|---|---|---|
| 3,903,549 | 9/1975 | Deyerle | 3/1.912 |
| 4,437,193 | 2/1984 | Oh | 3/1.912 |
| 4,563,778 | 1/1986 | Roche et al. | 623/22 |
| 4,596,580 | 6/1986 | Weill | 623/22 |
| 4,624,674 | 11/1986 | Pappas et al. | 623/22 |
| 4,632,111 | 12/1986 | Roche | 128/303 R |
| 4,666,450 | 5/1987 | Kenna | 623/22 |
| 4,681,589 | 7/1987 | Trunzo | 623/22 |
| 4,714,477 | 12/1987 | Fichera et al. | 623/22 |
| 4,718,911 | 1/1988 | Kenna | 623/22 |
| 4,770,659 | 9/1988 | Kendall | 623/22 |
| 4,784,663 | 11/1988 | Kenna | 623/22 |
| 4,798,610 | 1/1989 | Averall et al. | 623/22 |
| 4,840,632 | 6/1989 | Kampner | 623/22 |
| 4,851,006 | 7/1989 | Tuice | 623/22 |
| 4,878,916 | 11/1989 | Rhenler et al. | 623/22 |

FOREIGN PATENT DOCUMENTS

| | | |
|---|---|---|
| 0142759 | 5/1985 | European Pat. Off. |
| 0245527 | 11/1987 | European Pat. Off. ............... 623/22 |
| 2845231 | 5/1979 | Fed. Rep. of Germany. |
| 483980 | 10/1977 | U.S.S.R. |
| 2080118 | 2/1982 | United Kingdom. |

OTHER PUBLICATIONS

Socket Fixation Using a Metal-Backed Acetabular Component for Total Hip Replacement, The Journal of Bone and Joint Surgery, vol. 64-A, pp. 745-748.

Stress Distributions in the Acetabular Region I. Before and After Total Joint Replacement, 15 J Biomechanics 155-164 (Bergman Press Ltd., 1982).

Stress Distributions in the Acetabular Region II. Effects of Cement Thickness and Metal Backing of the Total Hip Acetabular Component, 15 J. Biomechanics 165-170.

Advances in Total Hip Replacement by W. Harris (Pergamon Press Ltd. 1982).

Primary Examiner—David J. Isabella
Attorney, Agent, or Firm—Gary L. Griswold; Walter N. Kirn; Stephen W. Bauer

[57] ABSTRACT

An acetabular implant comprising a metal cup shell (2) adapted for securing to the pelvic bone of a patient and a plastic insert (9) for receiving the ball portion of a hip joint. A cavity (4) of the metal cup shell (2) and the outre surface of the plastic insert (9) are dimensioned to allow a pressure fit of the plastic insert (9) within the cavity (4) at the body temperature of the patient. The inner surface (6, 8) of the metal shell (2) defining the cavity (4) is provided with one or more apertures (10, 16), e.g., a circumferential groove (10) and a radial groove (16), into which the plastic material of the insert (9) may flow when the insert (9) is fitted to provide a mechanical interlock between the insert (9) and cup shell (2), thereby securing the insert (9) against rotational and distractional forces relative to the metal cup shell (2).

14 Claims, 2 Drawing Sheets

ACETABULAR COMPONENT OF HIP JOINT PROSTHESIS

This is a continuation of application Ser. No. 07/394,742 filed Aug. 16, 1989 now abandoned.

FIELD OF THE INVENTION

This invention relates to a hip joint prosthesis and in particular to the acetabular component of a hip joint prosthesis.

BACKGROUND OF THE INVENTION

Prosthesis for the replacement of hip joints are well known. Originally, only the ball-end on the head of the femur could be replaced but it has since proved possible to replace either part of the hip joint i.e., the acetabular socket of the joint or the ball-end on the femur.

Known acetabular cup implants, which form the socket portion of an artificial hip joint, comprise a metal cup shell, which is secured within the acetabulum in the pelvic bone of a patient, and an inner liner of plastic material which provides a spherical bearing surface for receiving the ball portion of the joint. The metal cup shell may be provided with an external thread to facilitate anchorage to the pelvic bone or may be secured by other means such as cement or screws. The plastic insert may be secured within the metal cup shell by numerous methods e.g. a retaining ring, press-fitting or force-fitting portions of the liner into apertures within the shell and thermally fitting the liner.

Many of the known methods for securing the plastic insert within the metal cup shell suffer from the disadvantage that there are a limited number of rotational positions in which the insert may be placed. This can be a serious disadvantage in cases where the insert has an angled face and it may not be possible to achieve the required alignment of the bearing surface of the insert relative to the ball portion of the joint without movement of the metal cup shell. Adjustments of the metal cup shell are often impracticable, particularly when the shell is secured by cement or screws.

Thermal fitting of the plastic insert relies upon the expansion of the insert at the temperature within the body to generate a high frictional force between the surface of the insert and the surface defining bore of the metal cup shell. In practice the insert is dimensioned to allow insertion into the bore of the metal cup shell at room temperature or lower temperatures and after insertion the plastic material will expand at the body temperature (37° C.) such that the insert is a pressure fit within the bore. Unwanted movement of the insert is prevented by the frictional torque differential between the contacting surfaces of the metal cup shell and insert. While the thermal fitting of inserts has the advantage of allowing unlimited rotational position possibilities when fitting the insert thereby ensuring accurate alignment, the strength of the thermal fit has been questioned, particularly in the longer term, where creep of the plastic material can weaken the force between the contacting surfaces of the insert and metal cup shell. Severe weakening will allow rotational and/or distractional movement of the insert relative to the metal cup shell.

SUMMARY OF THE INVENTION

According to the present invention, an acetabular implant is provided comprising a metal cup shell adapted for securing to the pelvic bone of a patient and a plastic insert for receiving the ball portion of a hip joint. A hemispherical cavity of the metal cup shell and the outer surface of the plastic insert are dimensioned to allow an interference or pressure fit of the plastic insert within the cavity at the body temperature of the patient. The inner surface of the metal shell defining the cavity is provided with one or more apertures or grooves into which the plastic material of the insert may flow when the insert is fitted to provide a mechanical interlock between the insert and cup shell, thereby securing the insert against rotational and distractional forces relative to the metal cup shell.

The invention allows unlimited rotational positioning of the insert relative to the metal cup shell during fitting of the prosthesis. The provision of locking apertures or grooves in the surface of the metal cup shell provide areas into which the plastic material of the insert will flow or creep after fitting thereby locking the insert in place. The apertures may conveniently take the form of a circumferential or annular groove adjacent the open end of the cavity of the metal cup shell to provide resistance to distraction and one or more "radial" grooves providing resistance to rotation.

BRIEF DESCRIPTION OF THE DRAWINGS

The invention will now be described with reference to the accompanying drawings in which.

Corresponding reference numbers indicate corresponding parts throughout the several views of the drawings.

DESCRIPTION OF PREFERRED EMBODIMENTS

The metal cup shell implant generally shown at 2 may be fabricated from any metal or alloy which will not corrode in contact with body fluids and withstand the forces to which the joint is subjected. Suitable metals include stainless steel, titanium and alloys of titanium e.g. with aluminum and vanadium.

Figure 4:
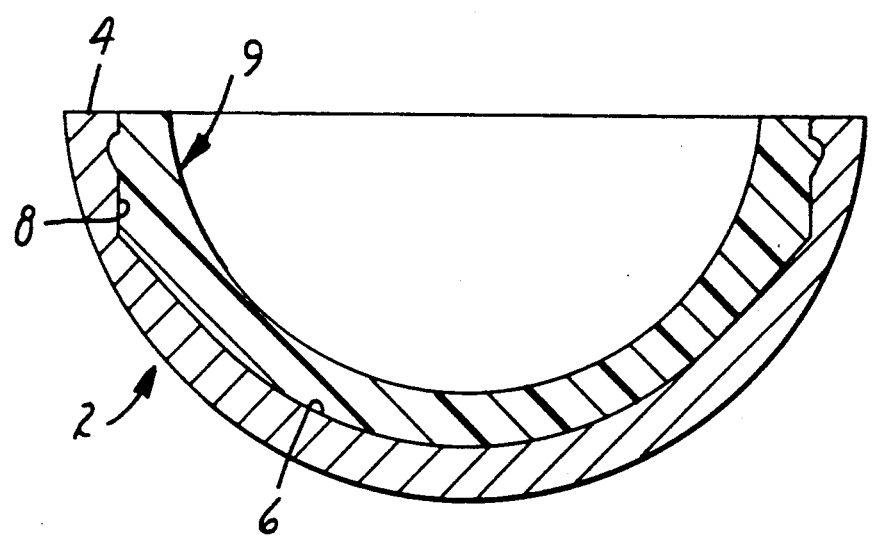
FIG. 4 is a cross-sectional view similar to FIG. 1 showing a plastic insert in the metal cup shell of FIGS. 1-3.

The metal cup shell implant 2 is generally hemispherical in shape and the outer surface may be provided with a thread or surface irregularities (not shown) to facilitate anchorage to the pelvic bone. Apertures (not shown) may be provided for inserting screws through the cup shell 2 into the pelvic bone. The generally hemispherical cavity 4 of the cup shell is defined by a substantially spherical inner surface 6 and a cylindrical or frusto-conical surface 8. A plastic insert 9 (FIG. 4) is generally fabricated from polyethylene and is provided with an outer surface which is an interference or thermal fit within the cavity 4 at the body temperature of the patient. The plastic insert 9 may readily be introduced at ambient temperature or at lower temperature e.g. after cooling with ice, and may be readily rotated within the cavity 4 to the desired position. As described above, the plastic insert 9 may be rotated within the cavity 4 during fitting. This is because the plastic material of the insert 9 does not fill or complement the locking circumferential or radial grooves 14 and 16 of the cup shell 2 until the plastic material deforms into the groove 16 due to creep or flow of the plastic material under pressure. When the insert 9 is raised to the body temperature thermal expansion of the insert causes an interference or pressure fit within the cavity 4. However, the implant 2 does not rely on the thermal friction fit between the surfaces of the insert 9 and cavity 4 of the metal cup shell 2 to prevent relative movement.

Figure 1:
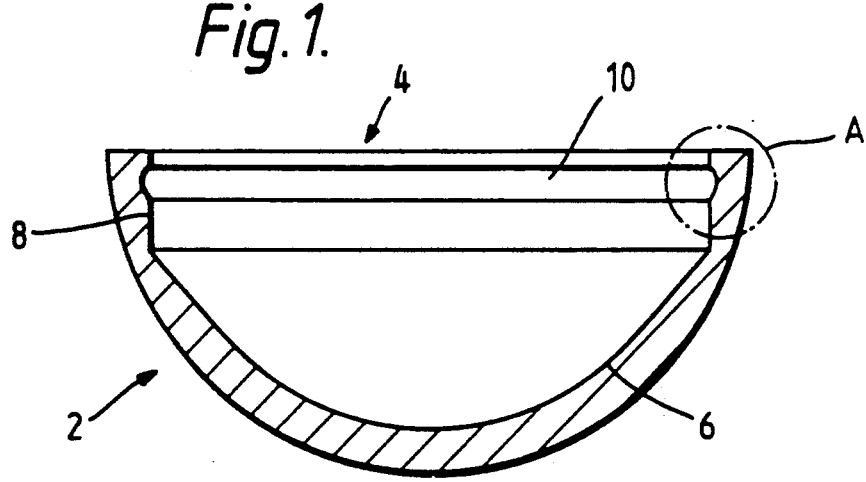
FIG. 1 represents a vertical section through a metal cup shell implant in accordance with the invention.
Figure 2:
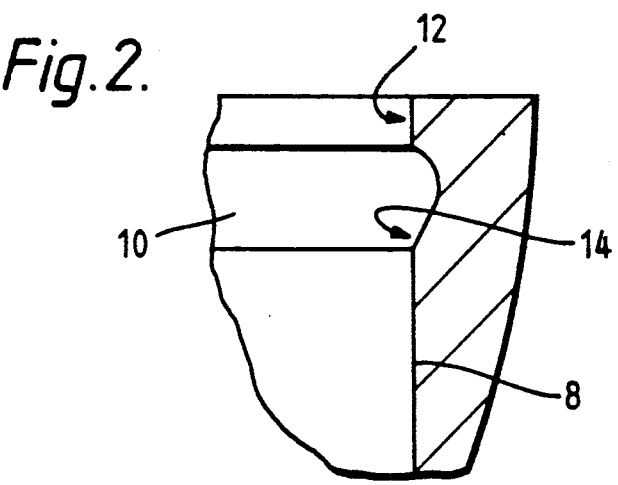
FIG. 2 represents an enlarged section of the area A in FIG. 1.
Figure 3:
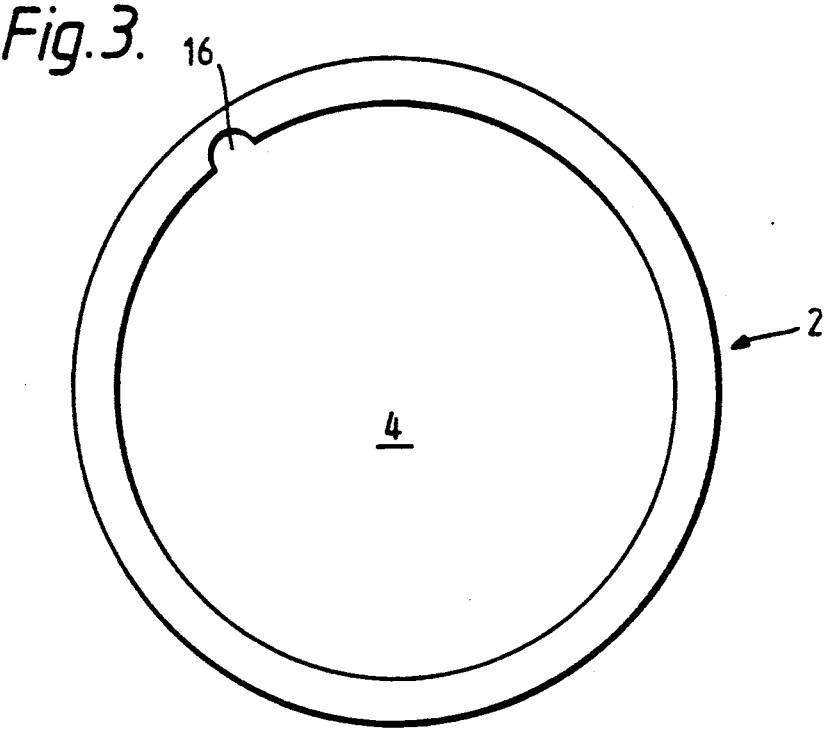
FIG. 3 represents a plan view of the metal cup shell of FIGS. 1 and 2.

Instead, the inner surface 6 or 8 of the cup shell 2 is provided with a generally circumferential or annular groove 10 into which the plastic material of the insert may flow or creep after fitting. The presence of the plastic material of the insert in the annular groove 10 provides a mechanical interlock thereby preventing removal of the insert from the cup shell 2. The cross-section of the annular groove 10 may be of any shape e.g. semi-circular, square, rectangular etc. A preferred cross-section for the groove 10 provides a one-way clutch effect by having a sharp corner of its leading edge 12 (nearer the opening of the cavity) and a chamfered trailing edge 14 (see FIG. 2). This arrangement allows the insert to slide into place, even with an interference fit, with the leading edge 12 providing a solid abutment against which the plastic insert material engages to prevent movement of the insert out of the cavity. The angle between the surface of the annular groove 10 and surface of the cavity at the leading edge 12 is preferably in the range 90° to 135° to provide a sharp corner.

In order to prevent rotation of the plastic insert after fitting, the inner surface 6 of the metal cup shell 2 is provided with one or more "radial" grooves 16. The radial grooves 16 may have any desired cross-section but are preferably symmetrical to provide equal resistance to rotation in either direction. The radial grooves 16 preferably have a sharp edge or lip on either side to provide high resistance to insert movement, and are conveniently semi-circular in cross-section.

It will be readily appreciated that the locking apertures or grooves 10 and 16 in the inner surface 6 and 8 of the cup shell 2 may have numerous configurations while providing resistance to both rotational and distractional movement of the insert. For example, discontinuous circumferential grooves will provide resistance to both types of movement as will square, hemispherical or elliptical apertures. However, it has been found that "radial" and "circumferential" continuous grooves may readily be provided in the inner surface 6 or 8 of the cup shell 2 during the fabrication process.

As various changes could be made in the above constructions and methods without departing from the scope of the invention, it is intended that all matter contained in the above description or shown in the accompanying drawings shall be interpreted as illustrative and not in a limiting sense.

I claim:

1. An acetabular implant kit adapted to be secured to the pelvic bone of a patient for receiving the ball portion of a hip joint, the kit comprising a metal cup shell adapted to be secured to the pelvic bone of a patient, and a plastic insert for receiving the ball portion of the hip joint, the plastic insert being formed of plastic material that is adapted to creep or flow under pressure at the body temperature of the patient, the metal cup shell having an inner surface defining a generally hemispherical cavity having an opening for receiving the plastic insert, the plastic insert having an outer surface that is dimensioned for a pressure fit within the cavity of the metal cup shell at the body temperature of the patient, the metal cup shell including walls defining at least one locking aperture or groove through the inner surface of the shell into which the plastic material of the plastic insert will flow after the insert is fitted to provide a mechanical interlock between the plastic insert and metal cup shell, thereby securing the plastic insert against rotational and distractional forces relative to the metal cup shell, the outer surface of the insert having an outer surface portion corresponding to the locking aperture or groove of the metal cup shell that does not complement the aperture or groove before fitting of the insert, the plastic insert being adapted to creep or flow under pressure such that the outer surface portion corresponding to the aperture or groove will deform into the aperture or groove after fitting the plastic insert in the metal cup shell, the opening of the hemispherical cavity defining a base plane, the metal cup shell having at least one generally radial groove formed in the walls of the metal cup shell constituting a locking groove, the radial groove defining a radial plane disposed at an angle to the base plane, the metal cup shell having at least one generally annular or circumferential groove defining a plane that is generally parallel and adjacent the base plane, the annular or circumferential groove defining a locking groove.

2. An acetabular implant kit adapted to be secured to the pelvic bone of a patient for receiving the ball portion of a hip joint, the kit comprising a metal cup shell adapted to be secured to the pelvic bone of a patient, and a plastic insert for receiving the ball portion of the hip joint, the plastic insert being formed of plastic material that is adapted to creep or flow under pressure at the body temperature of the patient, the metal cup shell having an inner surface defining a generally hemispherical cavity having an opening for receiving the plastic insert, the plastic insert having an outer surface that is dimensioned for a pressure fit within the cavity of the metal cup shell at the body temperature of the patient, the metal cup shell including walls defining at least one locking aperture or groove through the inner surface of the shell into which the plastic material of the plastic insert will flow after the insert is fitted to provide a mechanical interlock between the plastic insert and metal cup shell, thereby securing the plastic insert against rotational and distractional forces relative to the metal cup shell, the outer surface of the insert having an outer surface portion corresponding to the locking aperture or groove of the metal cup shell that does not complement the aperture or groove before fitting of the insert, the plastic insert being adapted to creep or flow under pressure such that the outer surface portion corresponding to the aperture or groove will deform into the aperture or groove after fitting the plastic insert in the metal cup shell, the metal cup shell and plastic insert being configured to allow unlimited rotational positioning of the plastic insert relative to the metal cup shell during fitting.

3. A kit according to claim 2 wherein the metal cup shell has at least one generally annular or circumferential groove generally parallel and adjacent the opening of the hemispherical cavity constituting a locking groove.

4. A kit according to claim 3 wherein the annular groove is continuous.

5. A kit according to claim 4 wherein the annular groove forms a sharp corner at the edge of the groove nearest the opening of the hemispherical cavity, and a chamfered edge opposite the edge having a sharp corner.

6. A kit according to claim 1 wherein the annular groove is continuous.

7. A kit according to claim 6 wherein the radial plane is generally perpendicular to the base plane.

8. A kit according to claim 6 wherein the annular groove forms a sharp corner at the edge of the groove nearest the opening of the hemispherical cavity, and a chamfered edge opposite the edge having a sharp corner.

9. An acetabular implant kit adapted to be secured to the pelvic bone of a patient for receiving the ball portion of a hip joint, the kit comprising a metal cup shell adapted to be secured to the pelvic bone of a patient, and a plastic insert for receiving the ball portion of the hip joint, the plastic insert being formed of plastic material that is adapted to creep or flow under pressure at the body temperature of the patient, the metal cup shell having an inner surface defining a generally hemispherical cavity having an opening for receiving the plastic insert, the plastic insert having an outer surface that is dimensioned for a pressure fit within the cavity of the metal cup shell at the body temperature of the patient, the metal cup shell including walls defining at least one locking aperture or groove through the inner surface of the shell into which the plastic material of the plastic insert will flow after the insert is fitted to provide a mechanical interlock between the plastic insert and metal cup shell, thereby securing the plastic insert against rotational and distractional forces relative to the metal cup shell, the outer surface of the insert having an outer surface portion corresponding to the locking aperture or groove of the metal cup shell that does not complement the aperture or groove before fitting of the insert, the plastic insert being adapted to creep or flow under pressure such that the outer surface portion corresponding to the aperture or groove will deform into the aperture or groove after fitting the plastic insert in the metal cup shell;

the opening of the hemispherical cavity defining a base plane, the metal cup shell having at least one generally radial groove formed in the walls of the metal cup shell constituting a locking groove, the radial groove defining a radial plane disposed at an angle to the base plane;

the radial plane being generally perpendicular to the base plane;

the radial groove having a generally semi-circular cross-section; and the metal cup shell having at least one generally annular or circumferential groove defining a plane that is generally parallel and adjacent the base plane, the annular or circumferential groove defining a locking groove.

10. A kit according to claim 9 wherein the annular groove is continuous.

11. A kit according to claim 10 wherein the annular groove forms a sharp corner at the edge of the groove nearest the opening of the hemispherical cavity, and a chamfered edge opposite the edge having a sharp corner.

12. A method of fitting an acetabular implant of the type adapted to be secured to the pelvic bone of a patient for receiving the ball portion of a hip joint, the method comprising the following steps:

securing a metal cup shell to the pelvic bone of a patient, the metal cup shell being of the type having an inner surface defining a generally hemispherical cavity having an opening for receiving the plastic insert and one or more locking aperture or groove through the inner surface of the metal cup shell;

providing a plastic insert of the type adapted for receiving the ball portion of the hip joint and having an outer surface that is dimensioned for a pressure fit within the cavity of the metal cup shell at the body temperature of the patient, the outer surface of the plastic insert having an outer surface portion corresponding to the locking aperture or groove of the metal cup shell that does not complement or fill the locking aperture or groove of the metal cup shell, the plastic insert being formed of plastic material that is adapted to creep or flow under pressure at the body temperature of the patient; and fitting the plastic insert in the metal cup shell including the step of inserting the plastic insert in the cavity of the metal cup shell and allowing the material of the plastic insert to creep or flow under pressure such that the outer surface portion corresponding to the aperture or groove of the metal cup shell deforms into the aperture or groove after fitting the plastic insert in the metal cup shell to provide a mechanical interlock between the plastic insert and metal cup shell, thereby securing the plastic insert against rotational and distractional forces relative to the metal cup shell.

13. A method according to claim 12 wherein the step of fitting the plastic insert includes cooling the plastic insert before inserting the plastic insert in the cavity of the metal cup shell.

14. A method according to claim 13 wherein the step of fitting the plastic insert includes rotating the insert relative to the metal cup shell after inserting the plastic insert in the metal cup shell before the material of the plastic insert has deformed into the aperture or groove of the metal cup shell.

* * * * *